United States Patent [19]

Eckenhoff et al.

[11] Patent Number: 4,781,714
[45] Date of Patent: Nov. 1, 1988

[54] DISPENSER FOR DELIVERING THERMO-RESPONSIVE COMPOSITION

[75] Inventors: J. B. Eckenhoff; Felix Theeuwes, both of Los Altos; Deters, Joseph C., Mountain View, all of Calif.

[73] Assignee: Alza Corporation, Palo Alto, Calif.

[21] Appl. No.: 916,581

[22] Filed: Oct. 8, 1986

Related U.S. Application Data

[63] Continuation of Ser. No. 547,885, Nov. 2, 1983, abandoned.

[51] Int. Cl.$^4$ ................................................ A61K 9/00
[52] U.S. Cl. .......................... 604/890.1; 604/892.1; 424/422; 424/424
[58] Field of Search .................. 604/890, 894, 892; 424/422, 424

[56] References Cited

U.S. PATENT DOCUMENTS

| | | | |
|---|---|---|---|
| 3,760,804 | 9/1973 | Higuchi et al. | 128/260 |
| 3,916,899 | 11/1975 | Theeuwes et al. | 128/260 |
| 3,995,632 | 12/1976 | Nakano et al. | 128/260 |
| 4,200,098 | 4/1980 | Ayer et al. | 128/260 |
| 4,235,236 | 11/1980 | Theeuwes et al. | 128/260 |
| 4,285,987 | 8/1981 | Ayer et al. | 427/3 |
| 4,309,966 | 1/1982 | Theeuwes | 128/260 |
| 4,327,725 | 5/1982 | Cortese et al. | 128/260 |
| 4,350,271 | 9/1982 | Eckenhoff | 222/386.5 |
| 4,439,195 | 3/1984 | Swanson et al. | 604/890 |
| 4,558,690 | 12/1985 | Joyce | 604/891 |
| 4,608,048 | 8/1986 | Cortese et al. | 604/890 |
| 4,612,008 | 9/1986 | Wong et al. | 604/890 |

FOREIGN PATENT DOCUMENTS

2161819  1/1986  United Kingdom ............... 604/890

*Primary Examiner*—Delbert R. Phillips
*Assistant Examiner*—Garnette D. Draper
*Attorney, Agent, or Firm*—Paul L. Sabatine; Edward L. Mandell; Steven F. Stone

[57] ABSTRACT

A dispenser is disclosed for delivering a beneficial agent formulation to a warm, fluid environment of use. The dispenser comprises an outer semipermeable wall surrounding and laminating an inner hydrophilic, swellable wall. The walls define an interior space for containing a thermo-responsive beneficial agent formulation. A passageway through the semipermeable wall connects the exterior of the dispenser through an opening in the inside wall with the interior of the dispenser.

14 Claims, 4 Drawing Sheets

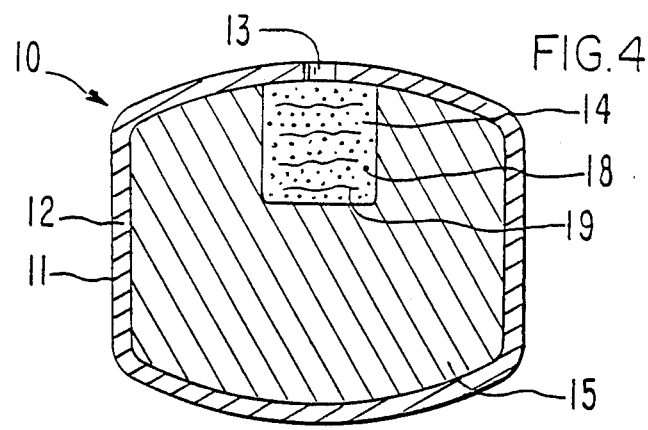
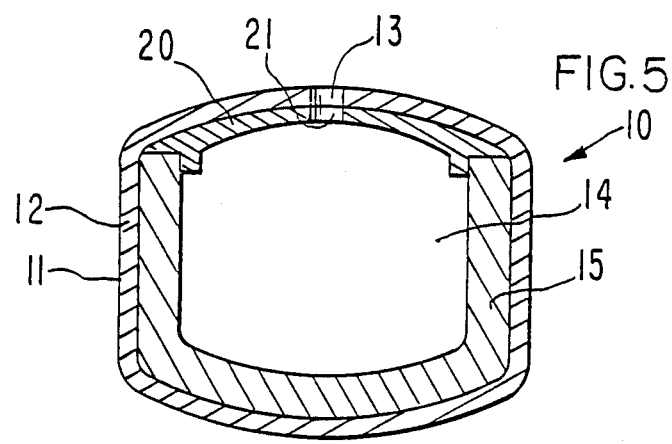
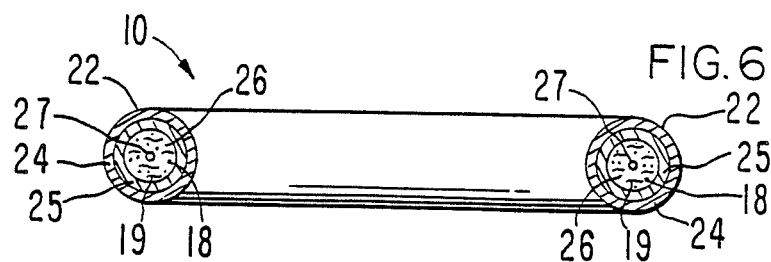
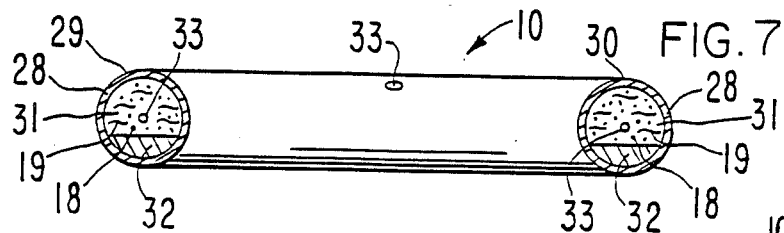
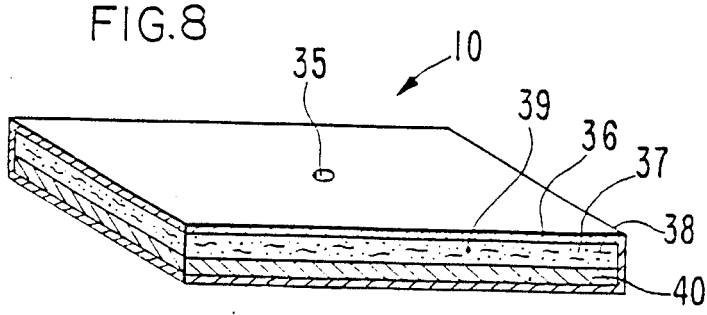
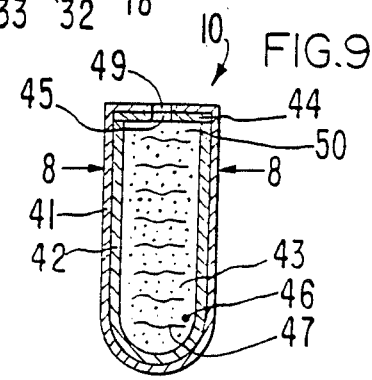

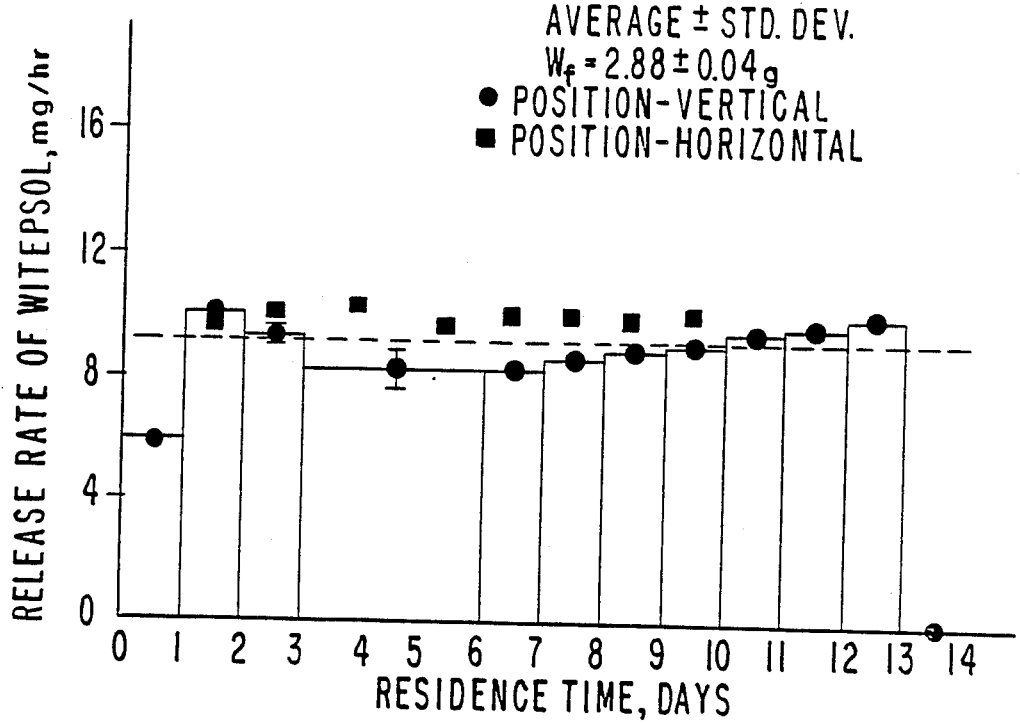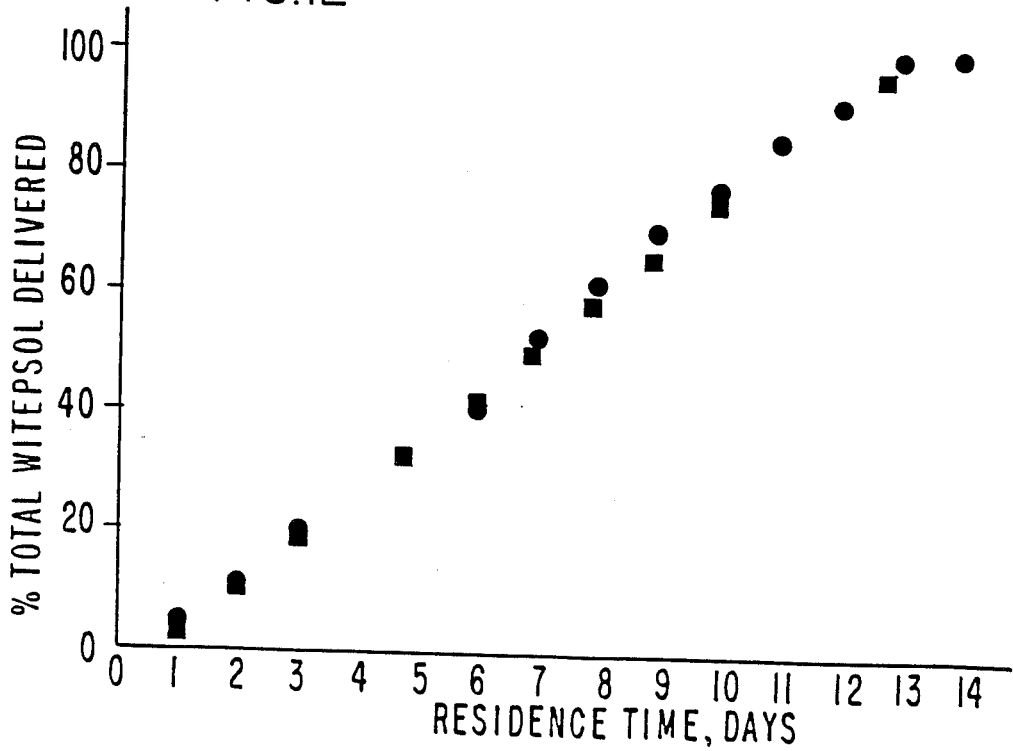

DISPENSER FOR DELIVERING THERMO-RESPONSIVE COMPOSITION

CROSS-REFERENCE TO RELATED APPLICATION

This application is a continuation of U.S. patent application Ser. No. 06/547,885 filed Nov. 2, 1983, now abandoned which application is incorporated herein by reference and benefit is claimed of its filing date.

AREA OF THE INVENTION

This invention pertains to both a novel and useful dispenser. More particularly, the invention relates to an osmotic dispenser for delivering a thermo-responsive composition containing a beneficial agent at a controlled rate to an environment of use over time.

BACKGROUND OF THE INVENTION

Dispensers for delivering a beneficial agent to an environment of use are known to the dispensing art. For example, U.S. Pat. No. 3,760,984 issued to patentee Theeuwes discloses a dispenser consisting of a heat shrinkable container carrying on its outer surface an osmotic solute and a distant layer of a polymer permeable to fluid. The dispenser has a plug for filling the container. The dispenser is powered by fluid being imbibed into the dispenser, wherein it dissolves the solute, thereby forming a solution that exerts pressure against the shrinkable container, causing it to shrink and deliver agent from the dispenser. In U.S. Pat. No. 3,865,108 patentee Hartop discloses a dispenser consisting of an inner collapsible tube containing a medicament disposed in a base member formed of a swellable material. The dispenser delivers the medicament by the base and parts absorbing fluid from the environment, thereby expanding and squeezing the collapsible tube causing the medicine to be expelled from the tube. In U.S. Pat. No. 3,971,376 patentee Wichterle discloses a dispenser consisting of a capsule having unitary walls formed of a cross-linked gel that is swellable in fluids. A textile fabric is imbedded in the material for imparting strength and minimizing problems due to poor mechanical properties associated with the material that show themselves during fluid uptake used to power the dispenser. In United States Pat. No. 3,987,790, patentees Eckenhoff et al disclose an improvement in an osmotic dispenser consisting of a conduit for filling a bag in the dispenser. The dispenser is powered by an osmotically effective solute imbibing fluid into the dispenser, which imbibed fluid generates hydraulic pressure that is applied against the bag, causing it to squeeze inwardly forcing agent from the dispenser. In U.S. Pat. No. 3,995,631, patentees Higuchi et al disclose a bag bearing on its outer surface a layer of an osmotic solute, and a distant wall formed of a material having part controlled permeability to fluid. In operation, a solution is formed of the solute, which solution squeezes the bag thereby causing delivery of the agent from the bag. In U.S. Pat. No. 4,320,758 patentees Eckenhoff et al disclose a dispenser consisting of a flexible bag, a sleeve made of a dispersion of an omsotically effective solute in a soluble polymer, and an outer wall permeable to fluid. The dispenser

OBJECTS OF THE INVENTION

Accordingly, it is an immediate object of this invention to provide a dispenser for delivering beneficial agents in all forms to environments of use, with a novel dispenser that represents an improvement in the dispenser art.

Another object of the invention is to provide a dispenser that is self-contained, self-starting, and self-powered in fluid environments, is easy to manufacture, and can be used for dispensing beneficial agents to animals, including humans, and to other biological and non-biological environments of use.

Another object of the invention is to provide a dispenser that can house a thermo-responsive, hydrophobic composition comprising insoluble to soluble drugs, and which thermo-responsive composition in response to the temperature of a biological environment changes its form and becomes fluid, semisolid, or the like for enhanced delivery from the dispenser.

Yet another object of the invention is to provide a dispenser comprising a lumen containing a temperature-sensitive composition, an expandable member partially surrounding the composition, an outer semipermeable wall surrounding the member and the lumen, and a dispensing passageway, and which dispenser delivers the composition by the combined physical-chemical operations of the composition melting and becoming fluid to semisolid or the like, the composition maintaining an immiscible boundary at the expanding member interface, and the expanding member swelling to displace an equivalent amount of composition from the dispenser. delivers drug by the sleeve imbibing water into the space between the outer wall and the bag, thereby exerting hydraulic pressure on the bag, which pressure causes the bag to be squeezed and delivers drug from the bag.

While the above dispensers are useful for delivering numerous agents to the environment of use, and while the dispensers represent a commercial advancement in the dispensing art, it will be appreciated by those skilled in the art that there are instances where a dispenser made with an inventively novel improvement would also enjoy wide commercial use and application in the dispensing art. For example, if a dispenser is made without a flexible bag and without a fabric member, thereby providing an improvement in the dispenser by reducing the number of steps and parts needed to make the dispenser, such a dispenser would have immediate acceptance, and it would also represent a major advancement in the art. Likewise, if a dispenser is provided that overcomes the prior art dispenser limitation of delivering agents only in solution or suspension forms, by the dispenser now delivering agents that are soluble or insoluble in fluid, semisolid or like forms, such a dispenser would enjoy instant appreciation and also represent a valuable contribution in the fields of science, medicine and commerce.

Yet another object of the invention is to provide a dispenser that is empty until filled with a solid composition that liquifies at elevated temperatures, and when filled can administer the composition that liquifies as a complete pharmaceutical dosage regimen for a period of time, the use of which requires intervention only for the initiation and the termination of the regime.

Yet another object of the invention is to provide a dispenser that can deliver beneficial drugs contained in a thermo-responsive, lipophilic pharmaceutically acceptable carrier that melts in the presence of thermal energy into a dispensable composition that is innocuous thereby substantially avoiding mammalian tissue irritation and interaction with mammalian protein tissue.

Still another object of the invention is to provide an osmotic dispenser containing a eutectic composition formed of at least two components and at least one drug, which eutectic composition has a melting point approximately the same as the temperature of a warm blooded animal, and is dispensed from the dispenser to the animal at said temperature.

Yet another object of the invention is to provide a dispenser that can house a thermo-responsive hydrophilic composition comprising insoluble to soluble drugs, and which thermo-responsive composition in response to energy input accompanying a biological environment of use changes its form and becomes dispensable for operative delivery from the dispenser.

Yet another object of the invention is to provide a dispenser that includes a beneficial agent that is chemically unstable in an aqueous environment and can be housed in the dispenser in a nonaqueous dispensing carrier, which agent is shielded in the nonaqueous carrier during delivery from the dispenser.

Other objects, features and advantages of the invention will be more apparent to those skilled in the dispensing art from the following detailed description of the specificiation, taken in conjunction with the drawings and the accompanying claims.

BRIEF DESCRIPTION OF THE DRAWINGS

In the drawings, which are not drawn to scale, but are set forth to illustrate various embodiments of the invention, the drawing figures are as follows:

FIG. 4 is a view of the opened dispenser of FIG. 3 illustrating the expansion of a driving member used for delivering a beneficial agent from the dispenser;

FIG. 5 is an opened view of FIG. 1 depicting a closure member in the lumen of the dispenser;

FIG. 6 depicts an embodiment of the invention wherein the members forming the dispenser are in concentric arrangement;

FIG. 7 depicts an embodiment of the invention wherein the members forming the dispenser are in partial circular sector arrangement;

FIG. 8 depicts an embodiment of the invention wherein the members forming the dispenser are in parallel arrangement;

FIG. 9 depicts an embodiment of the invention wherein the members forming the dispenser are in a pocket arrangement;

FIG. 11 is a graph that illustrates the rate of release per hour from a dispenser; and, FIG. 12 is a graph that illustrates the total amount of heat-sensitive composition delivered from the dispenser.

In the drawings and the specification, like parts in related Figures are identified by like numbers. The terms appearing earlier in the specification, and in the description of the drawings, as well as embodiments thereof, are further described elsewhere in the disclosure.

DETAILED DESCRIPTION OF THE DRAWINGS

Figure 1:
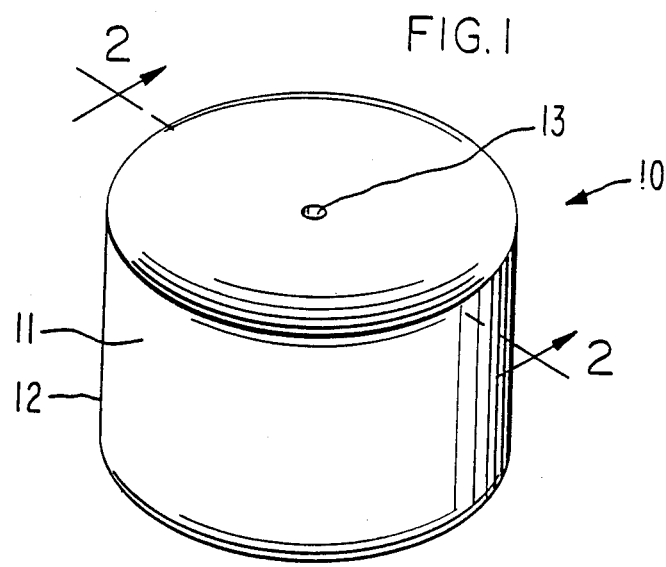
FIG. 1 is a view of a dispenser designed and manufactured for orally administering a beneficial drug to a warm-blooded animal.

Turning now to the drawings in detail, which are examples of new and useful dispensers for dispensing a beneficial agent, and which examples are not to be construed as limiting, one example of a dispenser is depicted in FIG. 1 by the numeral 10. In FIG. 1, dispenser 10 is seen comprising a body member 11, having a wall 12 and a passageway 13 in wall 12 that connects the exterior with the interior, as seen in FIG. 2, of dispenser 10.

Figure 2:
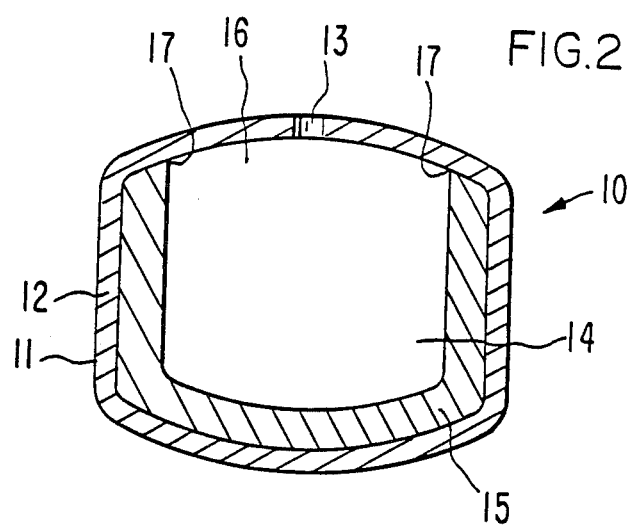
FIG. 2 is an opened view of the dispenser of FIG. 1 through 2—2 of FIG. 1 for illustrating the internal compartment and the thermodynamic members forming the device manufactured as an integral dispenser.

FIG. 2 is a cross-sectional view of FIG. 1 depicting dispenser 10 comprising body 11, wall 12 that surrounds an internal compartment 14 and a passageway 13 in wall 12 that communicates compartment 14 with the exterior of dispenser 10. Wall 12 is formed of a semipermeable polymeric wall forming composition that is substantially permeable to the passage of external fluid, and it is substantially impermeable to the passage of a beneficial agent and other ingredients contained in compartment 14. Wall 12 is non-toxic and it maintains its physical and chemical integrity during the life of dispenser 10.

Compartment 14 houses also a layer 15 of an expandable driving member that is in contact with the inside surface of wall 12. Interior layer 15 partially surrounds compartment 14, except for a mouth area 16 defined by spaced apart ends 17 of layer 15. Interior layer 15 has a shape that corresponds to the shape of semipermeable wall 12 and compartment 14. Layer 15 is made from a hydrogel composition, noncross-linked or optionally cross-linked, and it possesses osmotic properties, such as the ability to imbibe an exterior fluid through semipermeable wall 12 and exhibit an osmotic pressure gradient across semipermeable wall 12 against a fluid outside dispenser 10.

Figure 3:
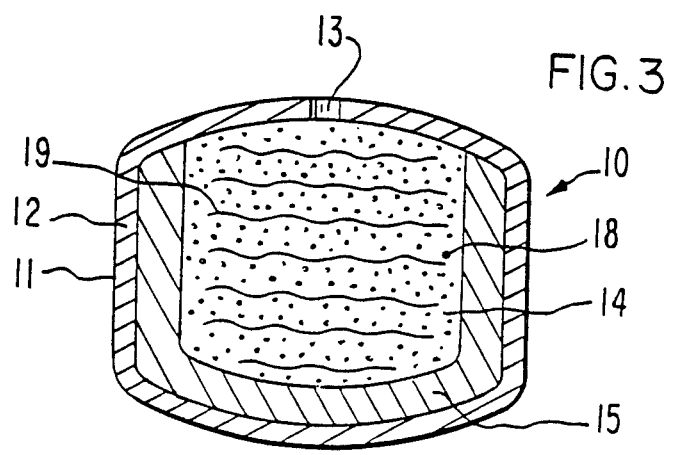
FIG. 3 is an opened view of the dispenser of FIG. 1 depicting the compartment of the dispenser charged with a temperature-sensitive composition containing a beneficial agent.

FIG. 3 depicts dispenser 10 of FIG. 1, is illustrated in opened cross-section. In FIG. 3, dispenser 10 embraces the structural members described for FIGS. 1 and 2, and it further illustrates dispenser 10 containing in compartment 14 a beneficial agent 18, identified by dots, and a thermo-responsive, heat-sensitive composition 19, (identified by wavy lines. Composition 19 is a delivery means and a transporting carrier for beneficial agent 18. The beneficial agent 18 housed in compartment 14 that can be delivered by dispenser 10 includes agents that are from insoluble to very soluble in both aqueous fluids and inlipophlic medium. The thermo-responsive composition 19, containing agent 18 homogenously or heterogenously dispersed or dissolved therein, if formed in a presently preferred embodiment of an anhydrous, heat sensitive, hydrophilic or hydrophobic material that exhibits solid-like properties at room temperature of 21° C., and within a few centigrade degrees thereof, and exhibits a melting point that approximates mammalian body temperature of 37° C., and with a few centigrade degrees thereof. The present invention uses the phrases "melting point", "softening point", or "liquifies" to indicate the temperature at which the thermo-responsive composition melts, undergoes dissolution, or dissolves to form a dispensable carrier so it can be used for dispensing agent 18 from dispenser 10.

In operation, when in the environment of use having a temperature of 37° C. within a few degrees, dispenser 10 delivers agent 18 by a combination of thermodynamic and kinetic activities. That is, in operation heat-sensitive composition 19 melts and forms a fluidic, a semi-solid, or a like deliverable phase, for delivering agent 18 through passageway 13. As composition 19 melts, fluid is imbibed through semipermeable wall 12 by hydrophilic layer 15 in a tendency towards osmotic equilibrium, to continuously swell, or expand and increase the volume of layer 15 and simultaneously layer 15 expands in compartment 14 while maintaining an intact immiscible boundary at the interface. Concomitantly, as layer 15 increases its volume, it applies pressure against composition 19 urging composition to decrease its volume. The simultaneous occurrences of the expansion of layer 15, the contraction of compartment 14, and the melting of composition 19 causes composition 19 containing agent 18 to be delivered through passageway 13 to the exterior of dispenser 10. FIGS. 3 and 4 considered together illustrate dispenser 10 in operation delivering agent 18. FIG. 3 depicts dispenser 10 at the beginning of an agent delivery period, and FIG. 4 depicts dispenser 10 nearing the end of an agent delivery period. The melting of composition 19, and the immiscibility of composition 19 add the expansion layer 15, the swelling and expansion of layer 15, with its accompanying increase in volume as seen in FIG. 4, along with the simultaneous corresponding reduction in volume of compartment 14 as seen in FIG. 4, assures the delivery of agent 18 at a controlled rate and continuously over time.

FIG. 5 is an embodiment of dispenser 10 of FIGS. 1 through 4, and it depicts additionally a closure 20 that fits into the open end of compartment 14. Closure 20 is sized and adapted to fit snugly into compartment 14 and it contacts the interior surface of layer 15. The exterior of closure 20 forms a fluid tight seal with the portion of the interior surface of layer 15 with which it contacts. Closure 20, optionally called a plug, has an axial, central bore 21 extending completely through closure 20. Bore 21 provides access to the interior of dispenser 10, mainly compartment 14, for filling compartment 14 with composition 19 containing beneficial agent 18. Concomitantly bore 219 provides access to passageway 13 in semipermeable wall 12 for dispensing composition 19 containing agent 18 from dispenser 10.

FIGS. 6 and 7 depict additional embodiments of dispenser 10 provided by the invention. In FIGS. 6 and 7, dispenser 10 is made in a presently preferred process of manufacture by coextruding the structural members forming dispenser 10. In FIG. 6, dispenser 10 is illustrated with its ends 22 and 23 opened for depicting the structure of dispenser 10. Dispenser 10 consists essentially of a semipermeable wall 24 that surrounds the complete exterior of dispenser 10, before its ends 22 and 23 are opened for illustrating the structure of dispenser 10, a middle swellable expandable push zone 25, and an inner thermo-responsive agent reservoir zone 26. Dispenser 10 further consists of a pair of delivery orifices 27 positioned in closed, surrounding semipermeable wall 24 for delivering a beneficial agent formulation from agent delivery closed ends 22 and 23, not seen in FIG. 6. FIG. 7 depicts dispenser 10 comprising a semipermeable wall 28 that surrounds and defines the exterior of dispenser 10, and is cross-sectioned at its ends 29 and 30 for depicting internal thermo-responsive agent reservoir 31 and a contacting layer of a swellable, expandable push member 32. Dispenser 10 has three delivery portals 33 through semipermeable wall 28 that communicate with agent reservoir 31 for dispensing the beneficial agent from dispenser 10. One portal is positioned in the body of dispenser 10 and the other two are positioned in the closed ends of dispenser 10. Dispenser 10 of FIGS. 6 and 7 operate as described above in the environment of use.

FIG. 8 depicts dispenser 10 manufactured in a rectangular shape; however, it is to be understood dispenser 10 can have other shapes that are sized and adapted for use in preselected fluid environments. In FIG. 8, dispenser 10 is opened along two of its boundaries, 9—9, for illustrating the internal arrangement of dispenser 10. Dispenser 10 comprises a delivery orifice 35, a semipermeable wall 36, a compartment 37 containing a thermo-responsive composition 38 containing beneficial agent 39, and a swellable, expandable push composition 40. Dispenser 10 operated for delivering agent 39 as described above, that is, thermo-responsive composition 38 melts in a temperature range of 35° to 41° C., and composition 40 in laminar arrangement expands and pushes composition 39 through orifice 35.

FIG. 9 illustrates a dispenser 10 that is capable of being manufactured in various sizes for uses as a dispensing pump. In the embodiment depicted, dispenser 10 is miniaturized for use as an implant dispenser for administering a beneficial agent to an animal. Dispenser 10 is seen in opened view along 8—8, and it comprises a shape-retaining wall 41 formed in at least a part of a semipermeable material that surrounds an inner, swellable pocket member 42. Pocket 42 is an opened container having an internal space 43 and an opening 50 that is suitably closed by closure 44. Closure 44 has an inlet-outlet, filling-dispensing hole 45 therethrough. Pocket 42 contains a beneficial agent 44 and a thermo-responsive carrier composition 47 therefor. A passageway 49 in simipermeable wall 41 aligns with hole 45 for filling dispenser 10 and for dispensing beneficial agent 46 from dispenser 10.

While FIGS. 1 through 9 illustrate various dispensers that can be made according to the invention, it is to be understood those dispensers are not to be construed as limiting the invention, as the dispenser can take a wide variety of shapes, sizes and forms for delivering beneficial agents to the environment of use. For example, the dispenser can be made for oral use having various conventional shapes and sizes such as round with a diameter of 3/16 inches to 1 inch. The dispenser can be adapted for use as a buccal, implant, artificial gland, cervical, intrauterine, ear, nose, dermal, vaginal, anorectal, rumen, such as the reticulum of cattle, and subcutaneous dispenser. The dispenser also can be shaped, sized and structured and adapted for delivering an active agent in streams, aquariums, fields, factories, reservoirs, laboratory facilities, hot houses, transportation means, hospitals, naval and military means, veterinary clinics, nursing homes, farms, zoos, sickrooms, chemical reactors, and other environments of use.

DETAILED DESCRIPTION OF THE INVENTION

In accordance with the practice of this invention, it has now been surprisingly found that dispenser 10 can be provided with a wall comprising a semipermeable material that does not adversely affect a host or animal, is permeable to the passage of an external aqueous type fluid, such as water and biological fluids, while remaining essentially impermeable to the passage of agents, including drugs, osmagents, and maintains its integrity in the presence of a thermotropic composition. The selectively, semi-permeable materials forming the outer wall are substantially insoluble in fluids, they are non-toxic, and they are non-erodible.

Representative materials for forming the semipermeable wall include semipermeable homopolymers, semipermeable copolymers, and the like. In one embodiment typical materials include cellulose esters, cellulose monoesters, cellulose diesters, cellulose triesters, cellulose ethers, and cellulose ester-ethers. These cellulosic polymers have a degree of substitution, D.S., on their anhydroglucose unit from greater than 0 up to 3 inclusive. By degree of substitution is meant the average number of hydroxyl groups originally present on the anhydroglucose unit that are replaced by a substituting group, or converted into another group. The anhydroglucose unit can be partially or completely substituted with groups such as acyl, alkanoyl, aroyl, alkyl, alkenyl, alkoxy, halogen, carboalkyl, alkylcarbamate, alkylcarbonate, alkylsulfonate, alkylsulfamate, and like semipermeable polymer forming groups.

The semipermeable materials typically include a member selected from the group consisting of cellulose acylate, cellulose diacylate, cellulose triacylate, cellulose acetate, cellulose acetate, cellulose diacetate, cellulose triacetate, mono-, di- and tri-cellulose alkanylates, mono-, di- and tri-alkenylates, mono-, di- and tri-aroylates, and the like. Examplary polymers including cellulose acetate having a D.S. of 1.8 to 2.3 and an acetyl content of 32 to 39.9%; cellulose diacetate having a D.S. of 1 to 2 and an acetyl content of 21 to 35%; cellulose triacetate having a D.S. of 2 to 3 and an acetyl content of 34 to 44.8%; and the like. More specific cellulosic polymers include cellulose propionate having a D.S. of 1.8 and a propionyl content of 38.5%; cellulose acetate propionate having an acetyl content of 1.5 to 7% and an acetyl content of 39 to 42%; cellulose acetate propionate having an acetyl content of 2.5 to 3%, an average propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate butyrate having an acetyl content of 2 to 29.5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate and the like; mixed cellulose esters such as cellulose acetate valerate, cellulose acetate succinate, cellulose propionate succinate, cellulose acetate octanoate, cellulose valerate palmitate, cellulose acetate heptonate, and the like. Semipermeable polymers are known in U.S. Pat. No. 4,077,407, and they can be made by procedures described in *Encyclopedia of Polymer Science and Technology,* Vol. 3, pages 325 to 354, 1964, published by Interscience Publishers, Inc., New York.

Additional semipermeable polymers include acetaldehyde dimethyl acetate; cellulose acetate ethylcarbamate; cellulose acetate methylcarbamate; cellulose dimethylaminoacetate; semipermeable polyamides; semipermeable polyurethanes; semipermeable polysulfanes; semipermeable sulfonated polystyrenes, cross-linked, selectively semipermeable polymers formed by the coprecipitation of a polyanion and a poly-cation as disclosed in U.S. Pat. Nos. 3,173,876; 3,276,586; 3,541,005; 3,541,006; and 3,546,142; selectively semipermeable silicon rubbers; semipermeable polymers as disclosed by Loeb and Sourirajan in U.S. Pat. No. 3,133,132; semipermeable polystyrene derivatives; semipermeable (polysodium styrenesulfonate); semipermeable poly (vinylbenzyltrimethyl) ammonium chloride; semipermeable polymers exhibiting a fluid permeability of $10^{-1}$ to $10^{-7}$ (cc.mil/cm$^2$.hr.atm) expressed as per atmosphere of hydrostatic or osmotic pressure difference across a semipermeable wall. The polymers are known to the art in U.S. Pat. Nos. 3,845,770; 3,916,899; and 4,160,020, and in *Handbook of Common Polymers,* by Scott, J. R. and Roff, W. J., 1971, published by CRC Press, Cleveland, Ohio.

The materials used for forming the swellable, expandable inner wall and the pocket, are polymeric materials neat, and polymeric materials blended with osmotic agents that interact with water or a biological fluid, absorb the fluid and swell or expand to an equilibrium state. The polymer exhibits the ability to retain a significant fraction of imbibed fluid in the polymer molecular structure. The polymers in a preferred embodiment are gel polymers that can swell or expand to a very high degree, usually exhibiting a 2 to 50 fold volume increase. The swellable, hydrophilic polymers, also known as osmopolymers can be noncross-linked or lightly cross-linked. The cross-links can be covalent or ionic bonds with the polymer possessing the ability to swell in the presence of fluid, and when cross-linked it will not dissolve in the fluid. The polymer can be of plant, animal or synthetic origin. Polymeric materials useful for the present purpose include poly(hydroxyalkyl methacrylate) having a molecular weight of from 5,000 to 5,000,000; poly(vinylpyrrolidone) having a molecular weight of from 10,000 to 360,000; anionic and cationic hydrogels; poly(electrolyte) complexes; poly(vinyl alcohol) having a low acetate residual; a swellable mixture of agar and carboxymethyl cellulose; a swellable composition comprising methyl cellulose mixed with a sparingly cross-linked agar; a water-swellable copolymer produced by a dispersion of finely divided copolymer of maleic anhydride with styrene, ethylene, propylene, or isobutylene; water swellable polymer of N-vinyl lactams; and the like.

Other gelable, fluid imbibing and retaining polymers useful for forming the hydrophilic, expandable push member include pectin having a molecular weight ranging from 30,000 to 300,000; gelatin having a viscosity of 15 to 30 millipoises and a bloom strength up to 150 grams; gelatin having a bloom value of 160 to 250; polysaccharides such as agar, acacia, karaya, tragacanth, algins and guar; Carbopol® acidic carboxy polymer and its salt derivatives; polyacrylamides; water-swellable indene maleic anhydride polymers; Good-rite® polyacrylic acid having a molecular weight of 80,000 to 200,000; Polyox® polyethylene oxide polymers having a molecular weight of 100,000 to 5,000,000; starch graft copolymers; Aqua-Keep® acrylate polymers with water absorbability of about 400 times its original weight; diesters of polyglucan; a mixture of cross-linked polyvinyl alcohol and poly(N-vinyl-2-pyrrolidone); zein available as prolamine; poly(ethylene glycol) having a molecular weight of 4,000 to 100,000; and the like. In a preferred embodiment, the expandable wall is formed from polymers and polymeric compositions that are thermoformable. Representative polymers possessing hydrophilic properties are known in U.S. Pat. Nos. 3,865,108; 4,002,173; 4,207,893; and 4,327,725; and in *Handbook of Common Polymers;* by Scott and Roff, published by Cleveland Rubber Company, Cleveland, Ohio.

The osmotically effective compound that can be blended homogenously or hetergenously with the swellable polymer, to form a push wall member, are the osmotically effective solutes that are soluble in fluid imbibed into the swellable polymer, and exhibit an osmotic pressure gradient across the semipermeable wall against an exterior fluid. Osmotically effective compounds are known also as osmagents. Osmotically effective osmagents useful for the present purpose include magnesium sulfate, magnesium chloride, sodium chloride, lithium chloride, potassium sulfate, sodium sulfate, mannitol, urea, sorbitol, inositol, succrose, glucose, and the like. The osmotic pressure in atmospheres, ATM, of the osmagents suitable for the invention will be greater than zero ATM, generally from zero ATM up to 500 ATM, or higher.

The swellable, expandable polymer, in addition to providing a driving source for delivering a beneficial agent from the dispenser, further serves to function as a supporting matrix for an osmotically effective solute. The osmotic solute can be homogenously or heterogenously blended with the polymer to yield the desired expandable wall or expandable pocket. The composition in a presently preferred embodiment comprises at least one polymer and at least one osmotic solute. Generally, a composition will comprise about 20% to 90% by weight of polymer and 80% to 10% by weight of osmotic solute, with a presently preferred composition comprising 35% to 75% by weight of polymer and 65% to 25% by weight of osmotic solute.

The term beneficial agent as used herein means any composition, formulation or compound that can be dispensed to produce a pre-determined beneficial and useful result. The beneficial agents include algicides, antioxidants, air purifiers, biocides, catalysts, chemical reactants, cosmetics, drugs, disinfectants, fungicides, foods, fertility inhibitors, fertility promoters, food supplements, fermentation agents, germicides, insecticides, microorganism attenuators, nutrients, plant growth promoters, plant growth inhibitors, preservatives, surfactants, sterilization agents, sex sterilants, vitamins, and other compositions that benefit the environment, surrounds, habitats and animals. The agent can be insoluble to very soluble in the temperature sensitive material housed in the dispenser.

In the specification and the accompanying claims, the term drug includes any physiologically or pharmacologically active substance that produces a local or systemic effect in animals, including warm blooded mammals, humans and primates, avians, pisces, household, sport and farm animals, laboratory animals, and zoo animals. The term physiological as used herein denotes the administration of a drug to produce normal levels and functions. The term pharmacological denotes variations in response to amounts of drug administered to the host. *Stedman's Medical Dictionary,* 1966, published by Williams and Wilkins, Baltimore, MD. The active drug that can be delivered includes inorganic and organic drugs, without limitations, those drugs that act on the nervous system, depressants, hypnotics, sedatives, psychic energizers, tranquilizers, anticonvulsants, muscle relaxants, antiparkinson agents, analgesics, anti-inflammatory, anti-malarials, hormonal agents, contraceptives, sympathomimetics, diuretics, anti-parasitics, neoplastics, hypoglycemics, ophthalmics, electro-lytes, diagnostics, and cardiovascular drugs. The amount of agent present in the dispenser can be from 0.05 ng to 20 g or more. For medical applications, the dispenser can contain various amounts, for example 25 ng, 1 mg, 5 mg, 125 mg, 250 mg, 500 mg, 750 mg, 1.5 g and the like. The dispenser can be used once, twice, or thrice daily; the dispenser can be used twice a week, and the like.

The term thermo-responsive as used for the purpose of this invention includes thermoplastic compositions capable of softening, or becoming dispensable in response to heat and hardening again when cooled. The term also includes thermotropic compositions capable of undergoing change in response to the application of energy in a gradient manner. These are temperature sensitive in their response to the application or withdrawl of energy. The term thermo-responsive as used for the purpose of this invention in a preferred embodiment denotes the physical-chemical property of a composition agent carrier to exhibit solid, or solid-like properties at temperatures up to 34° C., usually in the range of 20° to 33° C., and become fluid, semisolid, or viscous when disturbed by heat at temperatures from 33° C., usually in the range of 33° to 40° C. The thermo-responsive carrier is heat-sensitive and it has the property of melting, dissolving, undergoing dissolution, softening, or liquefying at the elevated temperatures, thereby making it possible for the dispenser to deliver the thermo-responsive carrier with the beneficial agent homogenously or heterogenously blended therein. The thermo-responsive carrier can be lipophilic, hydrophilic or hydrophobic. Another important property of the carrier is its ability to maintain the stability of the agent contained therein during storage and during delivery of the agent. Representative thermo-responsive compositions and their melting points are as follows: cocoa butter 32°-34° C.; cocoa butter plus 2% beeswax 35°-37° C.; propylene glycol monostarate and distearate 32°-35° C.; hydrogenated oils such as hydrogenated vegetable oil 36°-37.5° C.; 80% hydrogenated vegetable oil and 20% sorbitan monopalmitate 39-39.5%; 80% hydrogenated vegetable oil and 20% polysorbate 60, 36°-37° C.; 77.5% hydrogenated vegetable oil, 20% sorbitan trioleate and 2.5% beeswax 35°-36° C.; 72.5% hydrogenated vegetable oil, 20% sorbitan trioleate, 2.5% beeswax and 5.0% distilled water, 37°-38° C.; mono-, di-, and triglycerides of acids having from 8 to 22 carbon atoms including saturated and unsaturated acids such as palmitic, stearic, oleic, lineolic, linolenic and arachidonic; triglycerides of saturated fatty acids with mono- and diglycerides 34°-35.5° C.; propylene glycol mono- and disteartes 33°-34° C.; partially hydrogenated cottonseed oil 35°-39° C.; hardened fatty alcohols and fats 33°-36° C.; hexadienol and hydrous lanolin triethanolamine glyceryl monostearate 38° C.; eutectic mixtures of mono-, di-, and triglycerides 35°-39° C.; Witepsol ® #15, triglyceride of saturated vegetable fatty acids with monoglycerides 33.5°-35.5° C.; Witespol ® H32 free of hydroxyl groups 31°-b 33° C.; Witespol ® W25 having a saponification value of 225-240 and a melting point of 33.5-35.5%; Witespol ® E75 having a saponification value of 220-230 and a melting point of 37°-39° C.; a polyalkylene glycol such as polyethylene glycol 1000, a linear polymer of ethylene oxide, 38°-41° C.; polyethylene glycol 1500, melting at 38°-41° C.; polyethylene glycol monostearate 39°-42.5° C.; 33% polyethylene glycol 1500, 47% polyethylene glycol 6000 and 20% distilled water 39°-41° C.; 30% polyethylene glycol 1500, 40% polyethylene glycol 4000 and 30% polyethylene glycol 400, 33°-38° C.;

mixture of mono-, di-, and triglycerides of saturated fatty acids having 11 to 17 carbon atoms, 33°-35° C.; and the like. The thermo-responsive composition is a means for storing a beneficial agent in a solid composition at a temperature of 20°-33° C., maintaining an immiscible boundary at the swelling composition interface, and for dispensing the agent in a flowable composition at a temperature greater usually 33° C. usually 33°-40° C. The thermo-responsive composition on being dispensed into a biological environment are easily excreted, metabolized, assimilated, or the like for effective use of the beneficial agent.

The semipermeable wall can be applied to the expandable wall or pocket, to the laminated thermo-responsive lamina-expandable lamina, by molding, forming, spraying, or dipping into a semipermeable wall forming material. Other and presently preferred techniques that can be used for applying the semipermeable wall are the air suspension procedure and the pan covered procedures. This procedure consists in suspending and tumbling the laminate, or the pocket member in a current of air and a semipermeable wall forming composition until the wall surrounds and coats the member. The procedure is repeated with a different semipermeable wall forming composition to form a semipermeable laminated wall. The air suspension procedure is described in U.S. Pat. No. 2,799,241; *J. Am. Pharm. Assoc.*, Vol. 48, pages 451 to 459, 1979; and ibid, Vol. 49, pages 82 to 84, 1960. Other standard manufacturing procedures are described in *Modern Plastics Encyclopedia*, Vol. 46, pages 62 to 70, 1969; and in *Pharmaceutical Sciences*, by Remington, 14th Edition, pages 1626 to 1678, 1970, published by Mack Publishing Co., Easton, PA.

Exemplary solvents suitable for manufacturing the semipermeable wall include inert inorganic and organic solvents that do not adversely harm the materials, the expandable wall, the pocket, the thermo-responsive composition and the final dispenser. The solvents broadly include members selected from the group consisting of aqueous solvents, alcohols, ketones, esters, ethers, aliphatic hydrocarbons, halo-genated solvents, cycloaliphatics, aromatics, heterocyclic sol-vents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclo-octane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol. Generally, for the present purpose the semipermeable wall is applied at a tmperature a few degrees less than the melting point of the thermo-responsive composition. Or, the thermoplastic composition can be loaded into the dispenser after applying the semipermeable wall.

Figure 10:
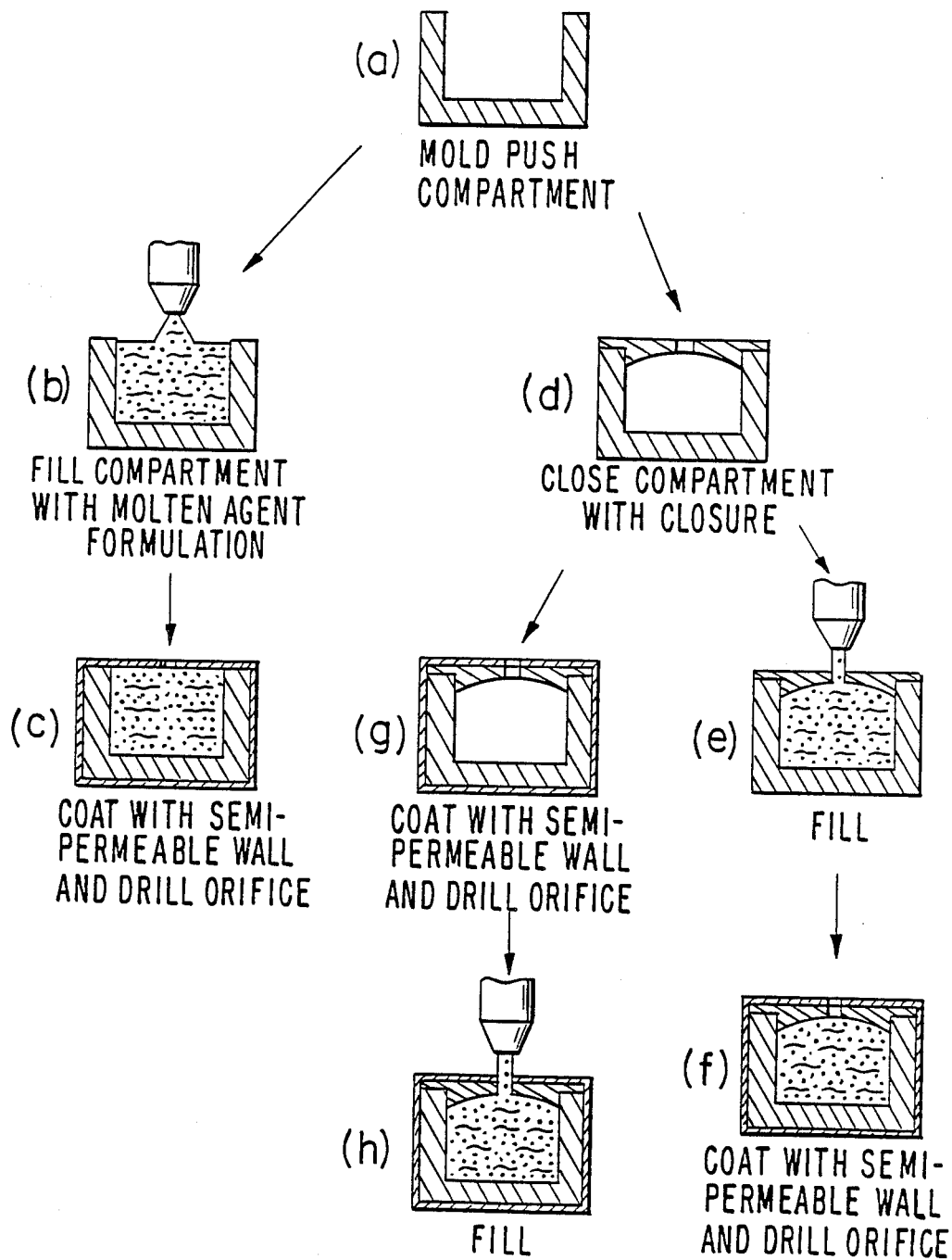
FIG. 10 is a flow diagram of three manufacturing processes used to make the dispenser provided by the invention.

The expandable wall, the pocket member, or the expandable lamina can be made by conventional thermoforming polymeric processes, such as spraying a mandrel, dipping a mold into a wall forming composition, blow molding, vacuum forming, compression molding, injection molding, extrusion and lamination. In one presently preferred embodiment, a pocket or expandable molded push compartment is made according to the compression process illustrated in FIG. 10. The process of compression molding consists in using a mold cavity and a plunger. A mold cavity forms one surface on the molded part and the polymeric wall forming composition is charged into the mold. The mold plunger forms the other surface of the pocket. The plunger compresses the polymeric composition when the mold is closed, and when the mold is closed the polymeric composition is compressed to the shape of the final pocket. The mold cavity and plunger are held in this position until the polymeric composition hardens. In FIG. 10, the pocket or molded push compartment is identified by the letter a, and it is seen on removal from the compression mold. Next, the pocket moves in one embodiment to a filling station, b, where it is positioned under a filling hopper and filled with a molten agent formulation. After cooling, the filled compartment is coated at c with a semipermeable wall and an orifice laser drilled through the semipermeable wall to yield a dispenser. In a similar process, the molded compartment a is closed at d with a closure made with a filling-discharge bore, and the closed compartment filled at filling station e at room temperature with a molten agent formulation. Finally, the filled compartment is coated at f with a semipermeable wall and an orifice laser drilled through the semipermeable wall in axial alignment with the bore to yield the dispenser. In a similar process, the closed compartment is coated with a semipermeable membrane (wall) and an orifice laser-drilled through the semipermeable wall in axial alignment with the bore to yield the empty dispenser identified by g. Then the dispenser is filled at room temperature with the molten agent formulation to yield the final operable dispenser h.

The expression orifice or passageway as used herein comprises means and methods in the semipermeable wall suitable for releasing a beneficial agent formulation from the dispenser. The orifice can be formed by mechanical or laser drilling, or by eroding an erodible element in the wall, such as a gelatin plug. A detailed description of orifices and the preferred maximum and minimum dimensions for an orifice are disclosed in U.S. Pat. Nos. 3,845,770 and 3,916,899.

DESCRIPTION OF EXAMPLES OF THE INVENTION

The following examples are merely illustrative of the present invention and they should not be construed as limiting the scope of the invention in any way, as these examples and other equivalents thereof will become more apparent to those skilled in the art in the light of the present disclosure, the drawings and the accompanying claims.

EXAMPLE 1

A dispenser is prepared as follows: first, an expandable capsule-shaped container is formed by injection molding a polymeric composition. The container has a diameter of 12 mm and a depth of 40 mm. The wall of the container is formed from a composition comprising 30% by wt of sodium chloride, and 70% by weight of poly(ethylene oxide) having a molecular weight of 3,000,000. The wall forming ingredients are blended in a commercial blender for 20 minutes to yield a homogenous composition. The composition is pressed into tablets and fed into an injection molding machine, and the container formed by injection molding at 145°-b 150° C. and at 6.5-7.0×10 kPa.

Next, the container is filled with a heat-sensitive composition comprising 0.5% by weight of theophylline, 77% by weight of hydrogenated vegetable oil, 20% by weight of sorbitan trioleate and 2.5% by weight of beeswax. The container is filled with the heat-sensitive drug composition at 36°-37° C. After cooling to 21° C., an outer semipermeable wall is applied to the filled container by coating in a Wurster air suspension coater. The semipermeable wall is formed from a 5% by weight, methylene chloride solution of cellulose acetate butyrate. The semipermeable wall is applied to a thickness of 0.4 mm, and the predispensers dried in an oven at 50° C. for 5 to 10 days. Finally, a 0.75 mm orifice is laser drilled through the semipermeable wall for dispensing the drug formulation from the compartment of the dispenser.

EXAMPLE 2

The container or wide mouth pocket is prepared according to Example 1 are filled with a drug formulation comprising 0.20 g of paracetamol, 0.02 g of codeine phosphate, 0.15 g acetylsalicylic acid and 2.0 g of Witepsol ® H35, a glycerol ester mixture of saturated vegetable fatty acids, in which lauric acid predominates. The composition is prepared by triturating and mixing well all the drug substances, and then adding the Witepsol carrier base at 38°-40° C. The pockets are filled with the molten composition and on cooling produce a creamy consistency. The pockets are coated with a semipermeable wall and an orifice laser drilled as previously described.

EXAMPLE 3

A dispenser having a compartment containing a thermo-responsive heat-sensitive composition in laminar arrangement with an expandable composition is made as follows: a mold is successive-ly charged first with a molten composition comprising 2.5% pheno-barbital, 20.5% glycergelatin and 77.0% of theobroma oil, a glyceride of stearic, palmitic and lauric acids, to form on cooling to room temperature the thermo-responsive lamina; then the mold is charged with a mixture of 30 parts of ethyleneglycol monomethacrylate containing 0.12 parts of ethyleneglycol dimethacrylate and 10 parts of 0.13% aqueous solution of sodium disulfate in aqueous ethanols. This mixture polymerizes at 30° C., and after 20 minutes following equilibration to room temperature the solid laminate is removed from the mold.

Next, a solution of cellulose acetate in acetone, 15 wt%, with an acetyl content of 39.8%, is prepared and the laminate coated by dipping into the solution for 15 times, first for a 10 second dip, then for 1 minute per dip, with an intervening 5 minute drying period. Following the dippings, the dispensers are dried at room temperature of 72° F. for 10 days. This procedure applies a 0.7 mm semipermeable rate controlling wall around the laminate. A passageway is laser drilled through the semipermeable wall connecting the exterior of the dispenser with the thermo-responsive lamina.

EXAMPLE 4

A dispensing device is prepared as follows: first, a heat-sensitive eutectic mixture of 77% neutral fat having a melting point of 35°-37° C. and 19.5% paraffin wax having a melting point of 52° C. is heated and liquified. To the liquid melt is added 3.5% of acetylsalicylsalicylic acid and the mixture poured into a mold. After cooling and solidification 500 mg of Cyanamer ® polyacrylamide, a hydrogel of approximately 200,000 mol. wt. is added to the mold and the layers pressed to form a thermo-responsive layer in contact with a hydrogel layer, and the contacting layers removed from the mold.

Next, a semipermeable wall is formed by blending 85 g of cellulose acetate having an acetyl content of 39.8 with 200 ml of methylene chloride and 200 ml of methanol, and spray coating the two layered compartment forming member in an air suspension machine until a 0.25 mm thick semipermeable wall surrounds the compartment. The devices are dried for two weeks and a 0.4 mm passageway is laser drilled through the semipermeable wall communicating with the heat-sensitive composition.

EXAMPLE 5

The procedure of Example 4 is repeated with the compositions as described, except for the thermo-responsive composition, which now comprises a polyoxyethylene ether of a partial ester of a fatty acid and a polyhydroxy cyclic inner ether containing drug. The polyoxyethylene ether has from 2 to 5 oxyethylene groups and the partial esters of fatty acids contain from 14 to 18 carbon atoms. The composition contains a drug, and the thermo-responsive composition melts rapidly and completely at body temperature to form a liquified composition for easy dispensing from the dispenser.

EXAMPLE 6

The procedures of Examples 4 and 5 are repeated for formulating a thermo-responsive composition comprising 85 mg of sorbitan monostearate hydroxypolyoxyethylene ether with 4 oxyethylene groups per mol having a melting point of 38° C., 5 mg of sorbitan monostearate hydroxypolyoxyethylene ether with 20 oxyethylene groups per mole, 5 mg of the fatty acid ester sorbitan monoricinoleate and 15 mg of sodium indomethacin.

EXAMPLE 7

A heat-sensitive composition for use in the dispenser of Example 1 is prepared by blending with heat 30% polyethylene glycol 1500, 30% polyethylene glycol 4000, 30% polyethylene glycol 400, 9% cocoa butter and 1% oxyprenolol hydrochloride. The composition exhibits a melting time of 15 to 20 minutes at 37° C.

EXAMPLE 8

An osmotic capsule in the shape of a thin-walled cylinder with a hemispherical bottom was injected, molded with a composition consisting essentially of 65% sodium chloride, 20% Polyox ®, a poly(oxyethylene) polymer having a molecular weight of about 200,000, and 15% polyethylene glycol 200,000. The injection conditions under which the capsule was molded were as follows:
nozzle temperature—180±20° C.
zone 1—off
zone 2—230±25° C.
zone 3—220±25° C.
hot tip temperature—180±25° C.
mold cavity temperature—18±3° C.
core pin temperature—8±3° C.

stopper plate temperature—8±3° C.
lamp time—13.5±2 sec
injection time—1.9±0.5 sec
injection speed—5±1
injection pressure—84±7 kg/cm$^2$
back pressure—42±7 kg/cm$^2$
cycle time—20 sec inside and outside diameter and inside and outside length were 1.17 cm and 1.33 cm, and 3.70 cm and 3.85 cm.

The osmotic capsule was filled with 2.88 g of H-15 Witespol glycerol ester of a saturated vegetable fatty acid containing 0.1% oil red dye. The prefilled osmotic capsules were coated in a pan coater, (Accela-Cota) with cellulose acetate butyrate in a solvent consisting of methylene chloride: ethanol, (95:5), until a semipermeable membrane of 0.5 mm thickness was applied uniformly thereto. The systems were dried at 55° C. for 7 days, and an exit port was drilled to 1 mm diameter. The systems were tested for their release rate. In the accompanying Figures, FIG. 11 depicts the rate of release of thermosensitive composition in mg/hr/day from the system. FIG. 12 depicts the cumulative amount of thermo-sensitive composition released expressed as percent total delivered from the system. The circles indicate release from the system in a vertical position, and the squares indicate release from the system positioned in a horizontal position.

An embodiment of the invention pertains to a method for administering a beneficial drug at a controlled rate to the vaginal passageway or to the ano-rectal passageway of a warm-blooded animal, which method comprises the steps of: (A) admitting into the passageway a dispenser comprising: (1) an inside wall formed of a swellable, expandable polymeric composition that surrounds and forms an internal compartment; (2) a mouth in the inside wall; (3) a beneficial drug formulation in the compartment comprising a dosage unit amount of drug for performing a therapeutic program and a heat-sensitive carrier melts or dissolves at body temperature and is a means for transporting the drug from the dispenser; (4) an outer wall surrounding the pocket and the mouth, the outer wall formed of a semipermeable polymeric composition permeable to fluid and impermeable to drug; and, (5) an orifice through the outer wall and communicating through the mouth with the internal compartment; (B) imbibing fluid through the semipermeable wall by the inside wall at a rate determined by the permeability of the semipermeable wall and the osmotic pressure gradient across the semipermeable wall causing the inside wall to swell and expand; (C) melting the drug formulation in the compartment to form a flowable formulation; and (D) delivering the beneficial drug formulation from the compartment by the inside wall swelling and expanding against the melted formulation causing the formulation to be dispensed in a therapeutically effective amount through the orifice at a controlled rate to the passageway to produce the desired medical effect over a prolonged period of 1 hour to months, preferrably 1 hour to 24 hours.

Inasmuch as the foregoing specification comprises preferred embodiments of the invention, it is understood that variations and modifications may be made herein in accordance with the inventive principles disclosed, without departing from the scope of the invention.

We claim:

1. A dispenser for delivering a beneficial agent formulation to an environment of use, wherein the dispenser comprises:
   (a) a compartment;
   (b) a beneficial agent formulation in the compartment, which formulation comprises:
      (i) a beneficial agent; and,
      (ii) a thermoplastic, lipophilic means for delivering the beneficial agent from the compartment, said means stable up to 33° C. and absorbing heat from the environment of use above 33° C. thereby forming a deliverable formulation comprising the beneficial agent;
   (c) a first wall that surrounds at least in part the compartment, said wall comprising hydrophilic means for absorbing fluid from the environment of use for expanding the wall into the compartment;
   (d) a second wall that surrounds the first wall, which second wall comprises at least in part semipermeable means for permitting the passage of fluid through the second wall; and,
   (e) at least one passageway in the second wall communicating with the compartment for delivering the beneficial agent from the dispenser.

2. The dispenser for delivering the beneficial agent according to claim 1, wherein the first wall comprises a port for delivering the beneficial agent from the compartment.

3. The dispenser for delivering the beneficial agent according to claim 1, wherein the first wall comprises a hydrogel and an osmotically effective solute.

4. The dispenser for delivering the beneficial agent according to claim 1, wherein the first wall comprises a hydrogel.

5. The dispenser for delivering the beneficial agent according to claim 1, wherein the first wall comprises a port with a closure with a passageway.

6. The dispenser for delivering the beneficial agent according to claim 1, wherein the second wall comprises a member selected from the group consisting of a cellulose ester, cellulose ether, cellulose ester ether, cellulose acylate, cellulose diacylate, cellulose triacylate, cellulose acetate, cellulose diacetate, cellulose triacetate, and cellulose acetate butyrate.

7. The dispenser for delivering the beneficial agent according to claim 1, wherein the first wall comprises poly(ethylene oxide).

8. The dispenser for delivering the beneficial agent according to claim 1, wherein the first wall comprises poly(ethylene oxide), polyethylene glycol, and an osmotically effective solute.

9. The dispenser for delivering the beneficial agent according to claim 1, wherein the means for delivering the beneficial agent from the compartment comprises a glycol of a fatty acid ester.

10. A dispenser for delivering a beneficial agent at a rate controlled by the dispenser to a biological environment of use comprising a fluid and a temperature greater then 33° C., the dispenser comprising:
   (a) a wall comprising at least in part semipermeable means for permitting fluid to enter the dispenser, which wall surrounds;
   (b) a compartment;
   (c) a first compostion in the compartment, which first composition comprises a beneficial agent and lipophilic carrier means for storing the beneficial agent, which carrier means changes to a dispensable composition when the dispenser is in operation in the biological environment;

(d) a second composition in the compartment, which second composition comprises hydrogel means for producing an expanding force when contacted by fluid that enters the compartment for pushing the changing first composition from the dispenser; and, (e) at least one passageway in the wall connecting the exterior of the dispenser with the interior of the dispenser for delivering the beneficial agent at a rate controlled by the combined operations of the dispenser to the biological environment.

11. A dispenser for delivering a beneficial agent to an environment of use comprising a fluid and a temperature corresponding to the temperature of a warm-blooded animal, the dispenser comprising:

(a) a wall comprising in at least a part a semipermeable polymeric composition, which wall defines a tube comprising an internal lumen;

(b) heat sensitive lipophilic means in the lumen for changing from a rested means to a dispensable means in response to the heat of the environment;

(c) a therapeutically effective amount of a beneficial agent in the heat-sensitive means;

(d) osmotic means for imbibing fluid through the wall into the lumen; which osmotic means surrounds at least in part the heat-sensitive means and in the presence of fluid applies an expanding force against the heat-sensitive means; and, (e) at least one passageway in the wall for connecting the exterior of the dispenser with the interior of the dispenser for delivering the beneficial agent from the dispenser over time.

12. The disenser for delivering the beneficial agent to the environment of use according to claim 11, wherein the tube comprises a closed end with a passageway.

13. A beneficial agent delivery device, the delivery device comprising:

(a) a body comprising a tubular shape and closed at its end, which body comprises a polymeric composition that lets an external fluid enter the device;

(b) a lumen in the body;

(c) a first layer in the lumen, said layer comprising a beneficial agent and a pharmaceutically acceptable carrier for the beneficial agent;

(d) a second layer in the lumen, said layer comprising a hydrogel composition that expands in the presence of fluid that enters the lumen and exerts a contacting force against the first layer; and, (e) at least one passageway in the body connecting the outside with the inside of the device for delivering the beneficial agent from the device.

14. A dispenser for delivering a beneficial agent formulation to an environment of use at a rate controlled by the dispenser, the dispenser comprising:

(a) a compartment;

(b) a beneficial agent in the compartmet;

(c) an inside wall that surrounds and forms the compartment, the wall comprising a composition that absorbs fluid and swells into the compartment;

(d) a port in the inside wall for filling and dispensing the beneficial agent;

(e) an outside wall that surrounds the inside wall, the outside wall comprising a composition that permits the passage of fluid and comprises a composition that is a member selected from the group consisting of plysulfone, polyacrylate, polymethacrylate, polymethylmethacrylate, and polyurethane; and, (f) at least one passageway in the outside wall for communicating with the port for dispensing the beneficial agent from the dispenser.

* * * * *